United States Patent [19]

Christensen

[11] Patent Number: Plant 6,823

[45] Date of Patent: May 30, 1989

[54] FLORIBUNDA ROSE PLANT CV. AROCRUBY

[75] Inventor: Jack E. Christensen, Ontario, Calif.

[73] Assignee: Bear Creek Gardens, Inc., Medford, Oreg.

[21] Appl. No.: 132,868

[22] Filed: Dec. 14, 1987

[51] Int. Cl.[4] ..... A01H 5/00

[52] U.S. Cl. ..... Plt./22

[58] Field of Search ..... Plt./22

*Primary Examiner*—Robert E. Bagwill

*Attorney, Agent, or Firm*—Majestic, Parsons, Siebert & Hsue

[57] ABSTRACT

This invention relates to a new and distinct variety of floribunda rose plant cv. Arocruby, particularly suited for garden decoration, identified by its white flowers which develop an intense red blush on those areas of the petals exposed to sunlight.

1 Drawing Sheet

The present invention relates to a new and distinct variety (cv. Arocruby) of rose plant of the floribunda class. The plant is a hardy outdoor seedling of the bush type cultivated for garden decoration. It was first originated by Jack E. Christensen in Ontario, Calif., U.S.A. under conditions of careful control and observation, and has as its seed parent the floribunda rose, Rumba (U.S. Plant Pat. No. 1,919) and, as its pollen parent, the floribunda rose Angel Face (U.S. Plant Pat. No. 2,792).

The new rose cv. Arocruby is particularly distinguishable from other commericalized rose cultivars by the following combination of characteristics: its white flowers which develop an intense red coloring on those portions of the petals exposed to sunlight; its large clusters of moderately sized flowers; and its stems which have virtually no large prickles and only a few small prickles.

Arocruby holds its distinguishing characteristics through succeeding propagations by budding.

The new variety cv. Arocruby may be distinguished from its seed parent, Rumba, by the following combination of characteristics: Whereas Rumba has flowers which are initially yellow in color and develop a red blush on those portions of its petals exposed to sunlight, the flowers of Arocruby are initially white in color and develop a red blush on those portions of its petals exposed to sunlight. The flowers of Rumba are borne in heavy, compact clusters whereas the heavy flower clusters of Arocruby are less compact. Whereas the mature plants of Rumba are average in size for the class, the plants of Arocruby are about $\frac{1}{2}$ to about $\frac{1}{3}$ times larger.

The new variety may be distinguished from its pollen parent, Angel Face, by the following combination of characteristics: Whereas the flower color of Angel Face is a deep mauve-lavender, the flower color of Arocruby is a combination of white with red. The flowers of Angel Face are borne in clusters of 3–4 individual flowers, whereas the flowers of Arocruby are borne in clusters of 6 to 8 or more individual flowers. Whereas the flowers of Angel Face are highly fragrant, the flowers of Arocruby are only slightly fragrant.

The accompanying drawing illustrates the new variety in color as grown in Somis, Calif., and shows the flowering thereof from bud to full bloom.

The descriptive matter which follows pertains to roses of the new variety grown outdoors in Somis, Calif., and is believed generally to apply to plants grown under similar conditions of soil and climate elsewhere. Plants and flowers of the new variety grown in other locations may vary in slight detail according to the climatic, soil and cultural conditions under which the variety is grown.

Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

FLOWERS

Flowers of the new variety are usually borne in flat clusters of 6 to 8 flowers per stem, sometimes 10 to 12 or more flowers per stem. Flower stems are of average strength and of average length for the class. The plant blooms very abundantly and continuously during the growing season, both outdoors and in the greenhouse. Flowers have a slight fragrance.

BUD

The penduncle is short to average in length for the class, of average caliper, and strong. The peduncle is moderately smooth with some stipitate glands and small prickles. Bud color is near Green 137D.

Before the calyx breaks, the bud is average in size for the class, of average length, pointed and ovoid to ovoid globular in form with a conspicuous neck. There are few foliaceous appendages and stipitate glands on the surface of the bud. Slender foliaceous parts extend beyond the tip of the bud equal to about $\frac{1}{4}$ to about $\frac{1}{2}$ of the bud length.

As the calyx breaks, petal color is near white. The inner surface of the sepals is lined with a fine wooly tomentum. Sepal margins are lined with stipitate glands, gland-tipped cilia and hairs.

As the first petal opens, buds are small to average in size for the class, average in length and pointed to ovoid in form. Color of the outside of the bud petals is a creamy white, near Yellow-White 158B with tints of green and red, near Green 142C and Red-Purple 63B. The inside surface of the bud petals is a creamy white, near White 158B in color.

The bud opens up well and is not prevented from opening by cold, hot, wet or dry weather.

BLOOM

The size of the bloom when fully open is average for the class, about $2\frac{1}{2}$ to about $2\frac{3}{4}$ inches in diameter. Petalage is double, averaging from about 27 to about 29 regularly arranged petals plus 1 to 2 petaloids.

Blooms at one half open are somewhat flat topped in form, with petals somewhat cupped. Petal edges are somewhat reflexed to rolled outward.

When fully open, the blooms are somewhat flat, with loosely cupped petals. Petal edges are somewhat undulated to rolled slightly outward.

The petals are of moderate substance, of average thickness, and slightly satiny on the inside and outside surface. Outside petals are nearly round to oval in shape, the rounded apices usually bearing 2 to 3 notches. Intermediate petals are nearly round to obovate in shape with rounded apices bearing 2 to 3 notches. Inside petals are obovate, with rounded apices bearing 2 to 3 notches.

Petal colors may be modified with other colors by being margined, shaded, or tinted with other colors.

The following paragraph describes the color values observed in a newly opened flower from a plant of the new variety grown in a greenhouse in Somis, Calif. in November of 1987.

The outside surface of the outside petals is near Red-Purple 63A in color on the upper half of the petal and near White 155B in color on the lower half of the petal. The inside surface of the outside and intermediate and inner petals is the same as the outside surface of the outside petals except that the red color occupies the upper $\frac{1}{4}$ of the petal, the balance of the petal being near White 155B. The outside surface of the intermediate and inner petals is near White 155B with a narrow red margin of near Red 63A.

The following paragraph describes the color values observed in a flower open for three days in a greenhouse from a plant of the new variety in November, 1987 at Somis, Calif.

The color of the outside surface of the outside petals is near White 155B. The inside surface of the outside petal is predominantly crimson red, near Red 63A, and a white at the petal base, near White 155B. The color of the outside and inside surface of the inside petal is near White 155B.

The general color effect of the newly opened flower is a pure white with bright, highly contrasting, red petal margins. The outside surface of the outer petals exposed to sunlight is mostly red.

After being open three days, the general color effect of the flower is a bright, crimson red blush over all petal surfaces exposed to sunlight. Those areas of the petal protected from exposure to sunlight remain a stark white.

Petals usually drop off cleanly, except for petaloids, and are not particularly affected by hot or wet weather.

Flowers grown in the month of November last 5 or more days on a bush in the garden. Cut flowers from rose plants grown in a greenhouse in November last from 6 to 7 days when kept at living room temperatures.

REPRODUCTIVE ORGANS

Stamens are few to average in number and are arranged irregularly about the pistils; a few may also be mixed with the petaloids. Filaments are medium in length and most have average to large sized anthers. Anthers open approximately all at once. Immature and mature anthers are near Greyed-Orange 164C in color. Pollen is produced in somewhat sparse quantities and is near Greyed-Orange 164C in color.

Pistils are few in number for the class (about 20). Styles are even, short in length, of average caliper, and are somewhat bunched. Stigma color is near Yellow 2D. Ovaries are usually enclosed in the calyx.

Hips are short in length for the class, oblong and gourd-shaped in form. Their flesh is moderately thin and their outside surface is smooth. Mature hips are near Orange 28B in color.

Sepals are permanent, and of average length for the class. The inside color of the mature sepals is near Greyed-Orange 177A. The outside color of the mature sepals is near Brown 200B.

Seeds are usually small and are few in number (about 5 to 7).

FOLIAGE

The compound leaves comprises 5 to 7 leaflets. Leaves are borne in normal quantities and are of average size for the class. Leaves are moderately heavy and are semi-glossy. Leaflets are oval in shape, with acute apices; their bases are round and their margins are serrate.

The color of the upper surface of mature leaves is near Green 139A. The under surface of the mature leaf is near Green 138C, washed with a reddish purple, near Greyed-Purple 186B. The upper surface of the young leaves is near Yellow-Green 147A, washed with Greyed-Purple 184B. The under surface of young leaves is near Greyed-Purple 184B in color.

The rachis is light to average in size. Its upper side is hairy with stipitate glands on the edges. The underside is moderately smooth with stipitate glands.

Stipules are average in length for the class and narrow, having short points turning out at an angle of less than 90°, slightly recurved toward the stem.

Plants of the new variety are average in their resistance to mildew and blackspot as compared with other cultivars now in commerce when grown under comparable conditions at Somis, Calif.

GROWTH

Plants of the new variety are average in height much branched and bushy in habit. Plant growth is moderately vigorous. Canes are of moderate to light caliper for the class.

The main stems are near Yellow-Green 144A in color. They bear no large thorns and few small prickles, near Greyed-Red 179D in color. There are no hairs.

Branches are near Green 138D in color; they bear no large thorns and few small prinkles, near Greyed-Red 179D in color. There are no hairs.

New shoots are near Yellow-Green 147A washed with Greyed-Purple 184B in color. New shoots bear no large thorns and few small prickles, near Greyed-Purple 184B in color. There are no hairs.

I claim:

1. A new and distinct variety of floribunda rose plant cv. Arocruby, and the parts thereof, being particularly characterized by its white flowers which develop an intense red coloring on those portions of the petals exposed to sunlight; its large clusters of moderately sized flowers; and its stems which have virtually no large prickles and only a few small prickles, substantially as described and illustrated herein.

* * * * *

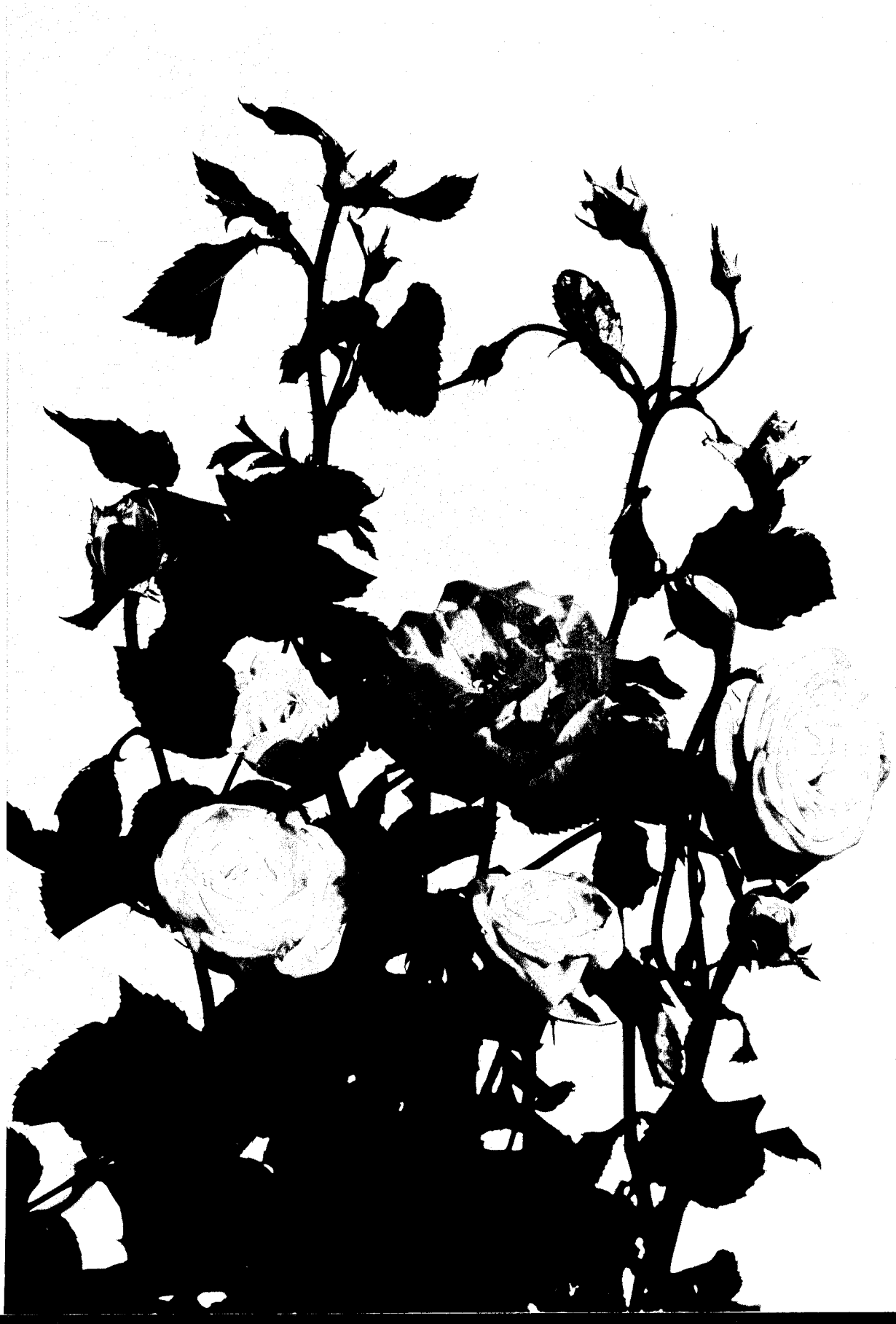

UNITED STATES PATENT AND TRADEMARK OFFICE

CERTIFICATE OF CORRECTION

PATENT NO. : Plant 6,823

DATED : May 30, 1989

INVENTOR(S) : Christensen

It is certified that error appears in the above-identified patent and that said Letters Patent is hereby corrected as shown below:

In the Abstract: insert --near-- before the words white flowers.

In Column 1, line 12 and line 36: insert --near-- before the word white; in line 24: replace "white" with --whitish--.

In Column 2, line 23: replace "penduncle" with --peduncle--; in line 36: replace "white" with --Red 63A--; in lines 42 to 43 and line 45: replace "a creamy" with --near--.

In Column 3, line 15: replace "oval" with --broadly obovate--; in line 48: replace "a pure" with --near--; in line 54: replace "a stark" with --near--.

In Column 4, line 45 should read: height --,-- much; in line 62: insert --near-- before the word white.

Signed and Sealed this

Fourth Day of December, 1990

*Attest:*

HARRY F. MANBECK, JR.

*Attesting Officer*

*Commissioner of Patents and Trademarks*